(12) United States Patent
Reinhardt (10) Patent No.: US 11,338,154 B2
(45) Date of Patent: May 24, 2022

(54) BACTERIA REMOVAL LASER

(71) Applicant: Ivoclar Vivadent AG, Schaan (LI)

(72) Inventor: Jonas Reinhardt, Igis (CH)

(73) Assignee: Ivoclar Vivadent AG, Schaan (LI)

(*) Notice: Subject to any disclaimer, the term of this patent is extended or adjusted under 35 U.S.C. 154(b) by 73 days.

(21) Appl. No.: 16/576,852

(22) Filed: Sep. 20, 2019

(65) Prior Publication Data

US 2020/0101315 A1 Apr. 2, 2020

(30) Foreign Application Priority Data

Sep. 28, 2018 (EP) .................................... 18197486

(51) Int. Cl.
| | | |
|---|---|---|
| *A61N 5/06* | (2006.01) | |
| *A61C 17/00* | (2006.01) | |
| *H01S 1/00* | (2006.01) | |
| *H01S 3/16* | (2006.01) | |
| *A61C 1/00* | (2006.01) | |
| *A61N 5/067* | (2006.01) | |

(52) U.S. Cl.
CPC .......... *A61N 5/0624* (2013.01); *A61C 1/0046* (2013.01); *A61C 17/00* (2013.01); *A61N 5/0603* (2013.01); *H01S 1/00* (2013.01); *H01S 3/1608* (2013.01); *H01S 3/1643* (2013.01); *A61N 5/067* (2021.08); *A61N 2005/0606* (2013.01); *A61N 2005/0628* (2013.01); *A61N 2005/0659* (2013.01); *A61N 2005/0665* (2013.01)

(58) Field of Classification Search
CPC ............ A61N 5/06; A61C 1/0046; A61L 2/00
See application file for complete search history.

(56) References Cited

U.S. PATENT DOCUMENTS

| | | | | |
|---|---|---|---|---|
| 4,983,381 A | * | 1/1991 | Torres Zaragoza | A61K 6/20 424/53 |
| 5,192,279 A | * | 3/1993 | Samuels | A61C 1/0046 606/16 |
| 6,193,711 B1 | | 2/2001 | Connors et al. | |
| 6,663,386 B1 | | 12/2003 | Moelsgaard | |
| (Continued) | | | | |

FOREIGN PATENT DOCUMENTS

JP 2002017757 A 1/2002

OTHER PUBLICATIONS

Brown et al. "Surface temperature and temperature gradients of human teeth in situ", Oct. 1966, Archives of Oral Biology, vol. 11, Issue 10, pp. 973-982; Abstract Attached. (Year: 1966).*

(Continued)

*Primary Examiner* — Lynsey C Eiseman
(74) *Attorney, Agent, or Firm* — Ann M. Knab; Thad McMurray (57) ABSTRACT

A bacteria removal laser is provided, especially for removing caries bacteria from natural or prosthetic teeth, the prosthetic teeth also being treated via extraoral approach, having a gripping handle, a laser radiation source, an application optics having a predetermined radiation exit surface, especially a radiation guide rod through which laser radiation passes, and an energy source such as a mains connection or an accumulator. The laser emits in the wavelength range between 2200 nm and 4000 nm and is especially designed as an Er:YAG laser. The energy output averaged over time is less than 1 mJ/mm² at the radiation exit surface.

13 Claims, 4 Drawing Sheets

(56) References Cited

U.S. PATENT DOCUMENTS

| | | | |
|---|---|---|---|
| 9,572,632 B2 | 2/2017 | Fotona | |
| 2003/0017073 A1* | 1/2003 | Eckhardt | A61L 2/10 422/24 |
| 2005/0245917 A1* | 11/2005 | Strassl | A61C 1/0046 606/17 |
| 2006/0206173 A1* | 9/2006 | Gertner | A61N 5/0616 607/88 |
| 2007/0282301 A1* | 12/2007 | Segalescu | A61N 5/062 604/509 |
| 2009/0061391 A1* | 3/2009 | Lukac | A61Q 11/00 433/215 |
| 2009/0075229 A1* | 3/2009 | Rizoiu | A61C 19/06 433/29 |
| 2010/0049180 A1* | 2/2010 | Wells | A61N 5/0616 606/12 |
| 2010/0168624 A1* | 7/2010 | Sliwa | A61N 7/022 601/3 |
| 2010/0234792 A1* | 9/2010 | Dacey, Jr. | A61B 5/0084 604/8 |
| 2011/0183283 A1 | 7/2011 | Strassl et al. | |
| 2011/0207075 A1* | 8/2011 | Altshuler | A61C 1/0046 433/29 |
| 2011/0217665 A1* | 9/2011 | Walsh | C03C 25/626 433/29 |
| 2012/0015318 A1 | 1/2012 | Kasenbacher et al. | |
| 2014/0141389 A1 | 5/2014 | Kalmeta | |
| 2016/0149369 A1* | 5/2016 | Monty | A61C 1/0046 372/35 |
| 2017/0215989 A1 | 8/2017 | Gregg, II et al. | |
| 2017/0273755 A1 | 9/2017 | Ertl et al. | |
| 2017/0274220 A1* | 9/2017 | Ertl | A61C 19/003 |
| 2018/0028276 A1 | 2/2018 | Sutter et al. | |

OTHER PUBLICATIONS

Lomke, DR. "The Safety and Effectiveness of Dental Er: YAG Lasers: A Literature Review With Specific Reference to Bone," Article, https://www.dentistrytoday.com/ce-articles/1368-the-safety-and-effectiveness-of-dental-eryag-lasers-a-literature-review-with-specific-reference-to-bone, 10 pages, Oct. 1, 2003.

* cited by examiner

BACTERIA REMOVAL LASER

CROSS-REFERENCE TO RELATED APPLICATIONS

This application claims priority to European patent application No. 18197486.6 filed on Sep. 28, 2018, the disclosure of which is incorporated herein by reference in its entirety.

TECHNICAL FIELD

The invention relates to a bacteria removal laser and a system directed to same.

BACKGROUND

It has been known for long to use bactericidal substances to combat bacteria that have attacked hard tissue and/or soft tissue in humans or animals.

Among them, there are especially antibiotics. Apart from the fact that antibiotics can result in resistance, antibiotics are unsuitable or ineffective if deep tissue layers are affected. This is especially true for hard tissue.

The hard tissues are mainly human and animal teeth. They are often affected by dental caries with caries bacteria, which especially include *Streptococcus mutans*.

Typically, dental caries is treated such that carious tooth material is removed with a conventional tooth drill.

Removal of the tooth hard tissue will damage the tooth. Nevertheless, it is required to remove slightly more than the affected carious tooth material, as a precaution, to ensure that no caries bacteria remain under the dental restoration that the dentist subsequently fabricates.

Other measures have also become known to prevent tooth decay. Among them, there are for example fluoridation with specific fluoride preparations and caries infiltration. In this case, low-viscosity plastic material is introduced into the carious tooth tissue and is intended to form a diffusion barrier.

Furthermore, covering with calcium hydroxide or glass ionomer cement has become known.

Furthermore, the use of laser light for caries treatment has been known for more than 20 years. According to EP 1 052 947 A1 and corresponding U.S. Pat. No. 6,663,386, which is hereby incorporated by reference, caries bacteria are to be vaporized using an Nd:wavelength laser. In order to achieve the desired effect, laser powers of 1 to 10 watts are used, so that the treatment surface can intensely be irradiated with the laser radiation with no depth effect.

Additionally, US 20170215989, US 20140141389, US 20120015318, US 20170273755, and US 20110183283 are directed to lasers used in dentistry and are hereby incorporated by reference.

Moreover, U.S. Pat. Nos. 6,193,711 and 9,572,632 are directed to lasers and are hereby incorporated by reference.

Testing laser light technology over the last 20 years has shown that it has no long-term success. While spread of caries appears to have been stopped on the surface, use of this technique will result in the caries to spread further in the long term, so that more radical measures will sooner or later be required, such as the replacement of the affected hard tooth substance by a tooth filling, an onlay or crown or root canal treatment.

If these measures are not taken, there will be a risk for the neighboring tooth and, where appropriate, the antagonist to also become affected by caries.

SUMMARY

In contrast, an object of the invention resides in creating a bacteria removal laser according to the claims, as well as a system consisting of a bacteria removal laser and a treatment surface according to the claims, which also have a long-term effect.

This and other objects will be solved by the claims. Advantageous further embodiments will arise from the subclaims.

According to the invention, the bacteria removal laser is designed as a hand-held device. Accordingly, it comprises a handle, which can be used to control the direction and the spatial positions of the laser radiation emission of the laser radiation source.

The laser radiation source can also be comprised in the handpiece, or at a fixed base station, which subsequently is connected to the gripping handle via a flexible radiation guide rod, if required. The griping handle also has a radiation exit surface, where the radiation emitted by the laser radiation source leaves the laser.

An application optics such as mirrors, lenses, fiber optics such as light guides, and the like, is also provided upstream or downstream of the radiation guide rod or on both sides thereof. This can, for example, be used for radiation equalization or, if necessary, for bundling the emitted radiation.

The laser emits in the wavelength range between 2200 nm and 4000 nm. An Er:YAG laser having an emission maximum of approximately 2940 nm is suitable for this.

Alternatively, GaInAsSb lasers, GaInSn lasers or GaInSb/GaSb lasers emitting between 2100 nm and 4000 nm are also available.

The laser can also work with a microwave emitter, e.g. in the frequency range between 2 and 3 GHz, and then forms a maser.

Lasers having large wavelength, i.e. in the long infrared range, are typically not recommended for use with the human body, as, for example, skin tends to burn at this wavelength during intense laser light application.

In addition, the current technical literature points out that laser radiation with a larger wavelength has a smaller penetration depth due to the absorption maxima of water that is present therein.

However, according to the invention, the bacteria removal laser has a wavelength and an energy output such as less than 1 $mJ/mm^2$, averaged over time.

Surprisingly, such laser exposure results in sustainable removal of bacteria. The exposure time for a correspondingly high penetration depth is at least several minutes, preferably 10 to 15 minutes.

The high absorption capacity of water at approximately 3000 nm is utilized. Due to laser application, the water evaporates at temperatures well below 100 degrees Celsius on the treatment surface and below it.

Obviously, the bacteria therein are also evaporated or at least are damaged.

When the water of the first layer has evaporated, for example within a layer thickness of 1 mm, the laser radiation, which is no longer absorbed by water, penetrates deeper and acting on the next millimeter of layer.

In this way, the laser radiation according to the invention is used for the removal of bacteria, until the caries bacteria, which populate deeper layers below the treatment surface, are also damaged.

According to the invention, it is advantageous to select the energy density and the power of the bacteria removal laser such that only a temperature increase of some degrees, for example a maximum of 8 or a maximum of 15 degrees, occurs at the tooth. Studies have shown that slow temperature increase is crucial to eliminate the risk of stress cracking in the tooth surface. The preferred temperature increase is less than 20 degrees/min, especially less than 15 degrees/min.

The targeted maximum temperature of the treatment surface is 45 degrees Celsius. Selection of a suitable pulse/pause ratio herein has a favorable effect. For example, the pulse/pause ratio may be 1 to 20 or 1 to 30. This represents a favorable compromise in this respect.

According to the invention, it is sufficient for the bacteria to be damaged such that they are no longer able to reproduce and can no longer produce "acid/metabolites".

It is not necessary to destroy the cell walls by vapor pressure, i.e. to make them burst by evaporation at 100 degrees Celsius, but it is sufficient to heat them to a considerably lower temperature, similar to pasteurization.

The inventive use of the bacteria removal laser also avoids the need of using a separate coolant. This eliminates the risk of thermal stresses and microcracks in the tooth surface. The absence of water cooling allows for high mobility of the laser.

Even though dental prostheses are, of course, never affected by caries, the bacteria removal laser according to the invention can also be used to "sterilize" them, because the bacteria found therein, which can also be *Streptococcus mutans*, for example, can also be damaged according to the invention.

This is particularly recommended for partial dentures because oral hygiene is particularly important for them.

A particular advantage of using laser radiation at about 3000 nanometers resides that both dentin and enamel are largely transparent to this wavelength. It is to be understood, that this does not apply to damp dental hard tissue. Water, and hence bacteria, absorb particularly well at this wavelength.

According to the invention, combination of these features can be utilized to easily reach even deep-seated bacteria through increased exposure time of the laser.

The laser radiation introduced becomes weaker as the penetration depth increases, if water and bacteria are present at that respective location. For example, absorption occurs with 15% to 25% per mm, or with 20% to 35% per mm penetration depth.

However, as removal of bacteria and drying of the tooth hard tissue increase, penetration depth increases so that the area where laser radiation attenuates is shifted further towards the inside of the tooth, i.e. towards the dentine.

This desired effect ensures even deep-seated bacteria to be removable.

Surprisingly, these deep-seated bacteria can also be rendered harmless.

It is advantageous for the bacteria removal laser to have a sensor designed to detect the radiation reflected from the treatment surface, or the radiation that passes through the treatment surface and underlying areas.

It is also possible to combine both types of detection.

It is a transmission sensor that is capable of detecting which radiation passes through the treatment surface and the areas below it, i.e. the treatment areas.

For example, increase in signal output of the sensor can be used to conclude that sufficient moisture and bacteria have been removed so that the treatment can be completed.

It is also possible to measure the pulsed laser radiation during pauses in radiation. In this case, the sensor detects the emission of the treatment surface in a suitable wavelength range between 1000 and 14000 nm, e.g. at 3000 nm, i.e. the temperature, e.g. of the tooth.

Preferably, the temperature is measured during irradiation, preferably in the wavelength ranges of 1-2.8 micrometers or 3.5-14 micrometers, i.e. outside the emission maximum of the Er:YAG laser.

Preferably, the bacteria removal laser has a control device. This is used to switch on the laser and either to cause it to emit for a specified, but preferably selectable period of time, or to shut the laser off when removal of caries bacteria has been completed.

In combination with the sensor, also the radiation can be reduced, for example, if the treatment surface has become too warm. In this case, the treatment time will automatically be extended.

The radiation exit surface is preferably smaller than a tooth. It can have a diameter of between 1 and 7 mm, it is preferred to be circular and to have a diameter of approximately 4 mm.

The laser according to the invention preferably is coupled with a sterile water source. This allows the treatment surface to be rinsed and simultaneously to be wetted following treatment so that accidental overdrying of the treatment surface can be avoided. The sterile water source can also be used downstream, when it is operationally associated to the laser, even if it is not installed therein.

According to the invention, there is also provided a system consisting of the bacteria removal laser and the treatment surface. The invention provides for the laser to emit radiation in the wavelength range between 1500 and 4500 nm, especially above 2200 nm, and directing it to the treatment surface.

During the beginning of the radiation emission the laser radiation is absorbed to 20 to 35% per mm penetration depth. In this way, it damages or destroys bacteria.

In one embodiment, the radiation reaches the treatment surface with an energy density averaged over time between $0.01$ $mJ/mm^2$ and $10$ $mJ/mm^2$.

In an embodiment, laser radiation is pulsed with the laser radiation source configured to emit with a pulse/pause ratio between 1:1 and 1:1000, with a power averaged over time of less than 2 W.

In another embodiment, laser radiation is pulsed with the laser radiation source configured to emit with a period duration between 0.02 s and 0.002 s, having an averaged power of less than 2 W, and having a switching device for switching the laser radiation source on and off with a frequency of less than 1 Hz, and/or having a treatment surface protection device, protecting the treatment surface from the radiation, with which the treatment surface is protectable from the radiation for a predetermined or adjustable or controllable time.

In another embodiment, laser radiation is pulsed with the laser radiation source configured to emit with a pulse/pause ratio between 1:5 and 1:200, with a power averaged over time of less than 2 W.

In another embodiment, laser radiation is pulsed with the laser radiation source configured to emit with a pulse/pause ratio between of about 1:25, with a power averaged over time of about 0.8 Watt.

In another embodiment, laser radiation is pulsed with the laser radiation source configured to emit with a period duration between 0.02 s and 0.002 s, comprising an averaged power of less than 2 W, and a switching device for switching the laser radiation source on and off with a frequency of less than about 0.3 Hz.

The invention enables the use of a bacteria removal laser to remove caries bacteria, especially removal of the metabolism thereof, genetic material thereof, and/or lethal removal thereof.

BRIEF DESCRIPTION OF THE DRAWINGS

Further advantages, details and features will arise from the following description of an example embodiment of the invention while making reference to the drawing, wherein.

DETAILED DESCRIPTION

Figure 1:
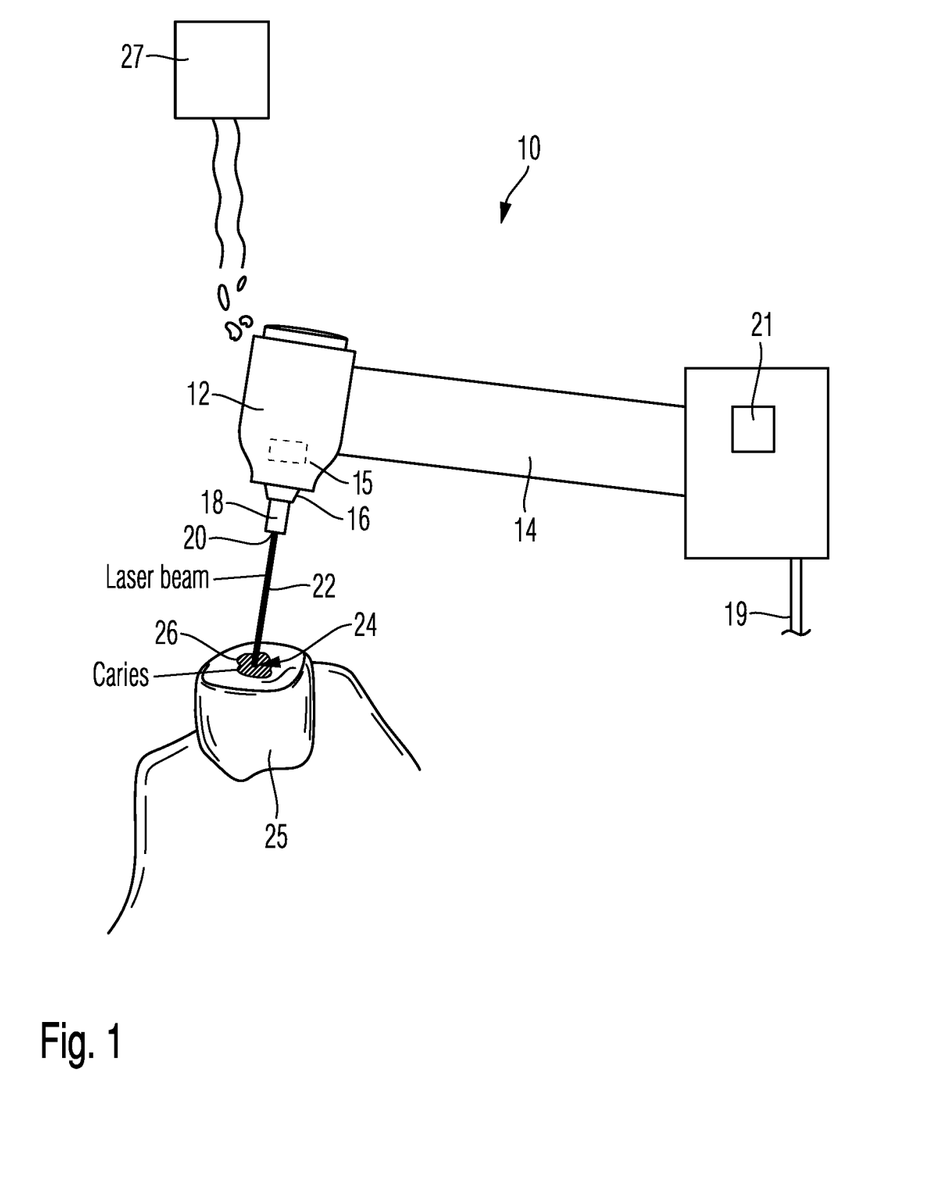
FIG. 1 is a bacteria removal laser according to the invention in schematic perspective representation, operable for the removal of caries bacteria in a first embodiment.

FIG. 1 is a bacteria removal laser in a first embodiment. The bacteria removal laser 10 comprises a radiation source 12, which is accommodated in a base station and is connected to a handheld device via a light guide, which, in addition, especially is heat-permeable. If necessary, the complete arrangement could also be realized in the head region of a handheld device. The handheld device has a gripping handle 14, which allows the user to bring it into the desired position.

In the head region of the handheld device application optics 16 are arranged which is passed through by the laser beam generated by the radiation source 12.

A radiation guide rod 18 is arranged terminating at a radiation exit surface 20.

The handheld device comprises a mains connection 19, which is the energy source such as an accumulator, and a control device 21. The energy source may be a wired or wireless source such as a battery supply or a rechargeable battery. Examples of accumulators include, but are not limited to, mainsprings, flywheel energy storage, hydraulic accumulators, rechargeable batteries, capacitors, and compensated pulsed alternators (compulsators). The control device can be a computer system, PLC (programmable logic controller), microcontroller, analogous control loops and the like.

The radiation source is formed as an Er:YAG laser emitting laser radiation with an emission maximum of 2940 nanometers.

The laser beam 22 hits a treatment surface 24, which, in this example, is formed on a molar 25, the occlusal surface of which is affected by caries 26.

In this example embodiment, the treatment surface is a circular area having a diameter of one millimeter. It is to be understood that the size of this surface can largely be adapted to the requirements. For example, the diameter may as well be as large as 5 mm.

The size of the treatment surface may also be designed to be adjustable. For this purpose, the application optics 16 has an appropriate adjustment mechanism to expand or reduce the optics focus.

The preferred size of the treatment surface is as large as the area typically affected by caries, for example 3 mm in diameter. If the diameter is smaller than the area affected by caries, the user is required to move the treatment surface across the entire area affected by caries so that treatment duration will increase.

According to the invention, the user of the laser according to the invention first checks which areas of tooth 25 are affected by caries, directing the laser radiation to such area in a manner known per se, i.e. as it is usually done with light curing devices, and turns on the handheld device.

The laser radiation is pulsed with a pulse pause ratio of 1:30.

Laser radiation is emitted with an energy density of less than 1 mJ/mm$^2$ averaged over time, hitting the treatment surface 24.

The user maintains this position for several minutes.

The pulsed laser radiation damages the caries bacteria in the area of the treatment surface 24. First, the focus is put on the superficial area of the treatment surface, i.e. slightly below the surface. The liquid which is present there, essentially saliva, evaporates so that the laser radiation penetrates deeper. Depending on the desired penetration depth, it is also possible to maintain radiation exposure for 15 or even 20 minutes.

Immediately below the treatment surface 24, tooth 25 comprises enamel. Caries bacteria have penetrated thereinto, typically 1 to 3 mm in depth, where they will cause caries, if the bacteria removal laser 10 is not used.

In an advantageous embodiment of the invention a supporting device is provided for the bacteria removal laser supporting at the jaw or chin of the patient.

The supporting device not shown herein is adjustable and allows for a position to be specifically adjusted, where the laser beam 22 hits the desired treatment surface 24.

The distance between the radiation exit surface 20 and the treatment surface 24 can also be adjusted using the support device. It is preferably between 1 mm and 2 cm.

After completion of the laser treatment, the area originally affected by caries bacteria is preferably rinsed with sterile water through the sterile water source 27. This compensates for loss of saliva during treatment and washes away dead bacteria.

Figure 2:
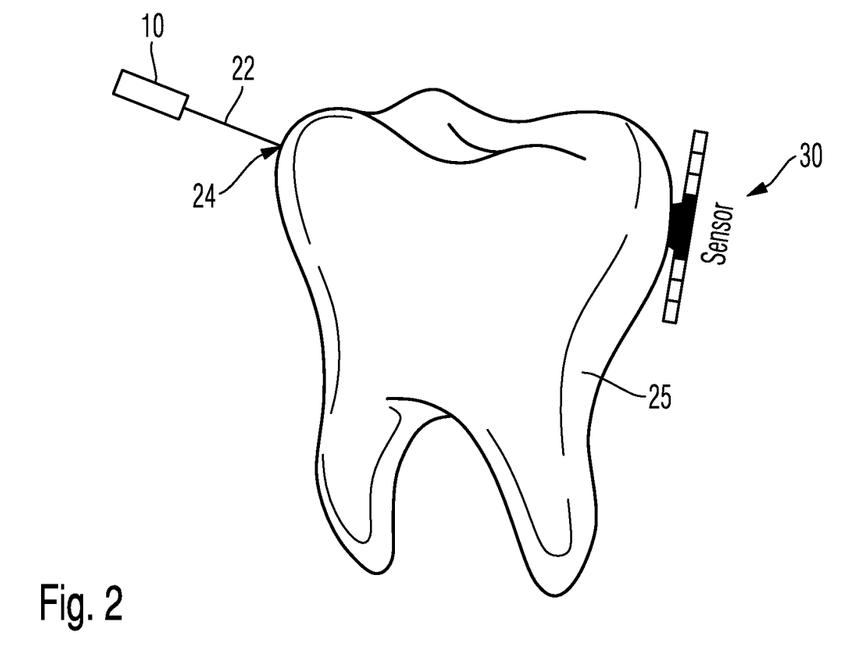
FIG. 2 is another embodiment of a bacteria removal laser comprising a sensor according to the invention.

FIG. 2 shows another embodiment of a bacteria removal laser according to the invention. A sensor 30 is attached to the side of a tooth 25 opposite to the laser 10. The sensor detects the laser radiation passing through the tooth 25. Specifically, a change in the laser radiation is detected.

Following absorption of the laser radiation in the area of the treatment surface 24 and decrease of the absorption in the course of the treatment due to evaporation of water or liquid therein, the output signal of the sensor increases.

An increase in an output signal can be used to conclude as to the progress of the treatment. For example, an increase of 3% can mean that 1 millimeter of penetration depth is now free of vital bacteria, and accordingly, an increase according to the Lambert-Beer law $$I(x)=I0*e-k*x,$$

means that the penetration depth now has increased accordingly.

According to FIG. 2, the sensor 30 is arranged outside the optical axis of the laser 10. This also can measure or sense scattering of the laser radiation in tooth 25.

Figure 3:
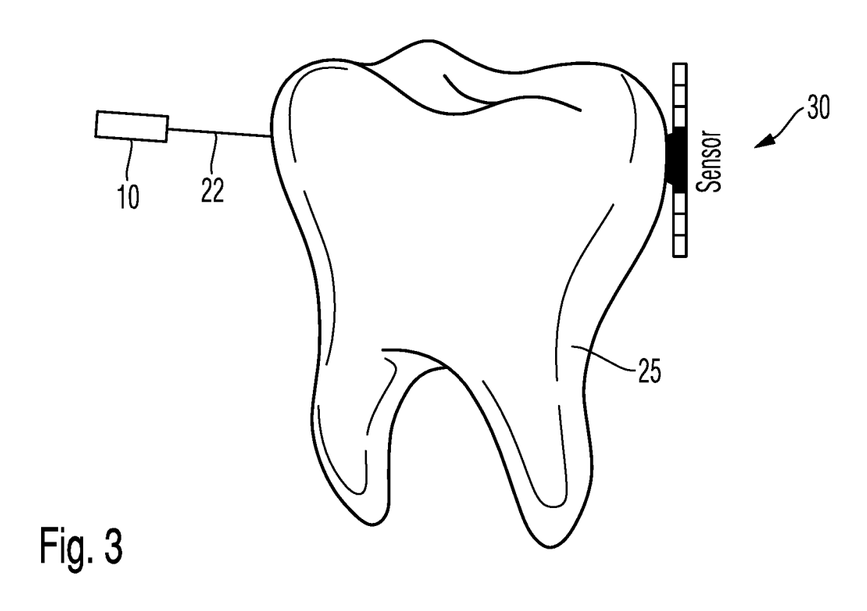
FIG. 3 is a third embodiment of a bacteria removal laser according to the invention.

According to FIG. 3, the laser is arranged in the optical axis so that laser radiation hits the sensor 30 directly following appropriate absorption.

The sensors 30 according to FIGS. 2 and 3 are designed as transmission sensors. Alternatively, it is also possible to implement a reflection sensor 15, as shown in FIG. 1.

Such a reflection sensor is focused directly onto the treatment surface 24. The reflection sensor detects drying of the treatment surface by the laser radiation, as a moist treatment surface 24 more strongly reflects than a dried one.

Figure 4:
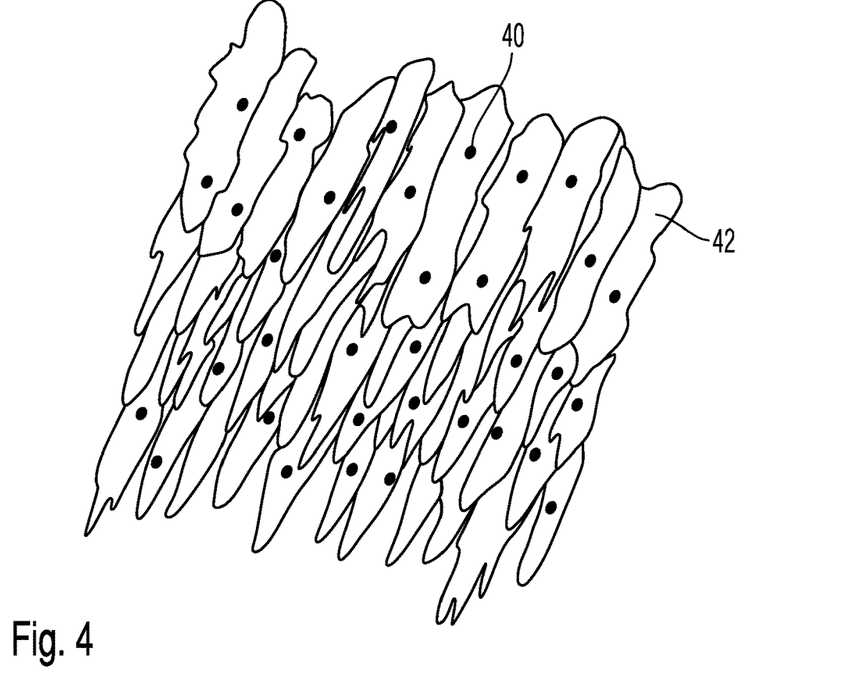
FIG. 4 is a schematic representation of a hard tissue with bacteria shown.

From FIG. 4, exemplary embedding of caries bacteria 40 in a hard tissue 42 can be seen. In this example, the hard tissue is tooth enamel, into which both liquid and bacteria can penetrate. The crystal structure of the enamel allows caries bacteria to spread in three dimensions, with penetration usually starting at the tooth surface.

Typically, the bacteria density is higher at the tooth surface, however, for successful caries removal it is required for the few deep-located bacteria to be damaged at least to the extent that they are no longer able to reproduce. This can be realized with bacteria removal laser according to the invention.

The sensors 30 shown in FIGS. 2 and 3 can measure at the wavelength of the laser 10. Alternatively and preferably, they are temperature sensors 30 arranged at any suitable location, which measure in pulse pauses and/or at wavelengths above or below the laser wavelength. The temperature sensors can be located at any suitable location.

Suitable low-price temperature sensors are able to detect in the wavelength range of between 1200 and 2500 nm.

Figure 5:
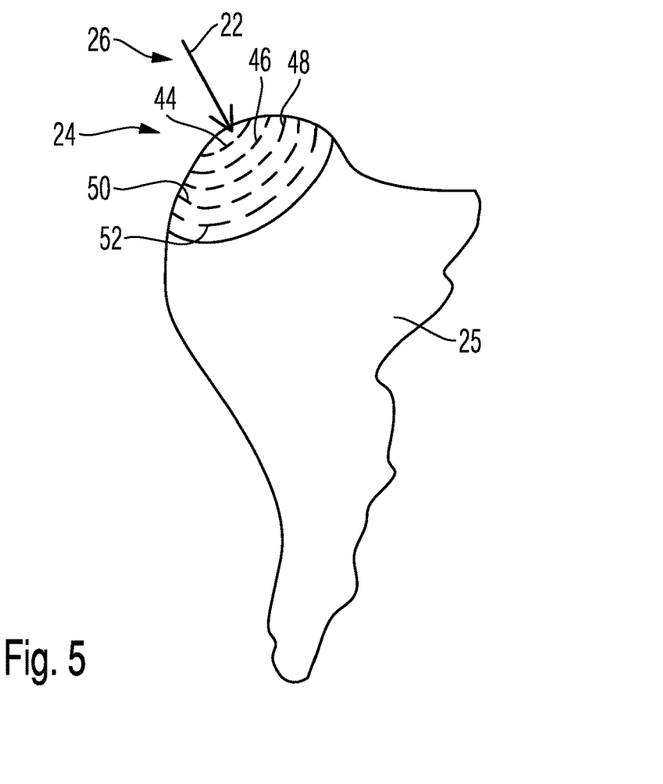
FIG. 5 shows the increasing penetration depth of the laser beam into the hard tissue.

FIG. 5 shows how exposure to bacteria damaging wavelengths advances. Initially, a first layer 44 is hit by the laser beam 22 directly adjacent to the treatment surface 24. Bacteria existing therein will be damaged.

Damage can be such that the cell walls are destroyed, but any other removal is also possible, for example complete removal of cell fluid by laser radiation.

As soon as the moisture content of the first layer 44 is significantly reduced, a large part of the laser radiation 22 reaches the area of the second layer 46. This procedure will also be repeated in the third, fourth and fifth layers 48, 50 and 52, until the bacteria in the entire caries affected area 26 will be destroyed or damaged.

The control device 21 controls the radiation source 12 such that caries bacteria are first damaged in the upper layers of the tooth 25. Those layers will be heated to dry, so that with laser power being the same, the temperature rise therein will increase.

The radiation source 12 is preferably operated in the pulse mode. It is also switched on and off periodically, e.g. every 3 seconds.

After a certain time has passed, all caries bacteria in layer 44 are destroyed. From this point, the second layer 46 will be removed, and so on.

The temperature of the tooth 25, especially the treatment surface 24, is constantly measured by sensor 30 or by another sensor.

If the temperature rise exceeds a threshold, this means that the caries bacteria are removed. This can be derived from the temperature gradient monitored by the control device 21.

Exemplary operating data of a bacteria removal laser according to invention 10 are listed below:

| Laser Er:YAG, The wavelength of the laser light is 2940 nm | |
| --- | --- |
| 0.26 mJ/mm$^2$ | Energy density, averaged |
| 50-100 Hz | Frequency laser pulses |
| 3-5 mm | Treatment surface |
| 1-20 min | Treatment duration |
| 21.7 W | Pulse maximum power |
| 30-300 μs | Pulse width |
| 0.5-2 W | Average laser power |
| Non pretreatment, no drilling required | |

In another embodiment of the invention, the following operating data were used:

| Laser Parameter | |
| --- | --- |
| Wavelength | 2.94 μm |
| I | 300 A |
| Frequency | 150 Hz |
| tp | 150 μs |
| Diameter focus | 4 mm |
| Surface | 12.6 mm$^2$ |
| Laser power | 0.72 W |
| Energy density | |
| Period | 6.67 ms |
| Duty Cycle | 2.25% |
| Peak Power | 0.0048 _W*s |
| Peak Power per surface | 0.000382 J/mm$^2$ |
| | 0.3820 mJ/mm$^2$ |
| Energy density | |
| Energy density | 0.00038197 J/mm$^2$ |
| | 0.382 mJ/mm$^2$ |
| Peak Power | |
| Peak Power | 32 W*s |
| Energy per Peak | |
| Energy per Peak | 0.0048 J |
| Power density | |
| Power density | 0.0573 W/mm$^2$ |
| Average Power | |
| P average (on full Period) | 0.72 W |

Furthermore, the theoretical removal or killing rate of the caries bacteria was calculated:

Their diameter is between approximately 0.1 and 700 μm, in most of the known species it is about 0.6 to 1.0 μm. Their length is in a larger range: for single cells it is between approximately 0.6 μm (for cocci) and 700 μm, hyphae may even be still longer, most bacteria are 1 to 5 μm in length. The volume of most bacteria is in the order of 1 μm$^3$.

| Bacterium assumed | |
| --- | --- |
| Volume | 1 μm$^3$ |
| Radius | 0.620 μm |
| Diameter | 1.24 μm |
| Density, Water | 1 g/cm$^3$ |
| Mass | 1E−12 g |
| Mass, Bacterium | 1.0E−06 μg |
| Temperature | 298 K |
| Hv | 44.0 kJ/mol |
| 100% Water10$^{-6}$ μg | 2.45E−09 J |

At 1 W 408,869,870 Bakterien/Sec

This means that about 2.5E-09 W*s=2.5E-09 joules are required to vaporize a bacterium. Assumption: 100% water and 100% of the energy is converted into evaporation enthalpy. Thus, with 1 watt, about 400 million bacteria could be evaporated per second.

Figure 6:
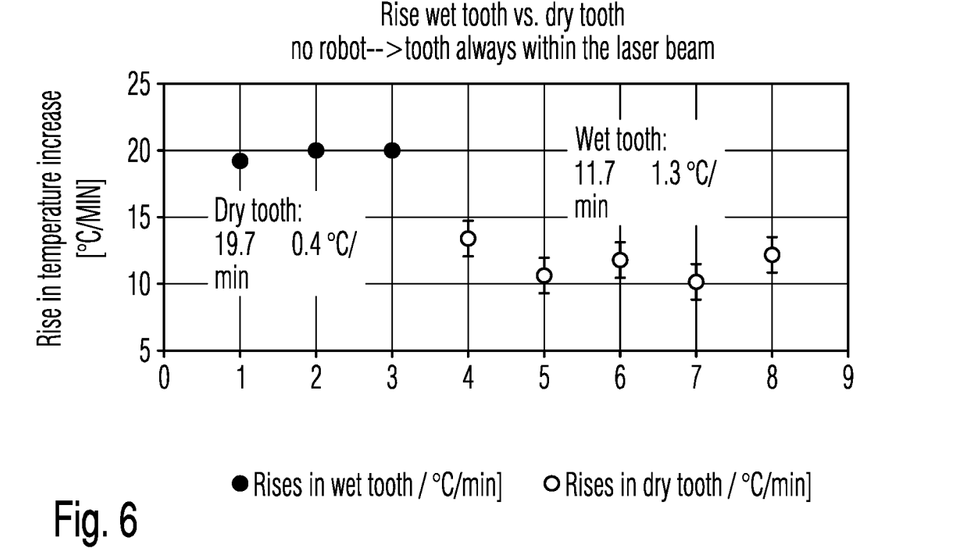
FIG. 6 is a diagram of the temperature increase measured for wet teeth compared to dry teeth.

FIG. 6 shows the temperature increase measured during operation of the bacteria removal laser 10 in comparison between "wet" and "dry".

A dry tooth was taken and the typical laser parameter (see above) was applied. At the same time, the temperature was measured. The heating rate (slope) in degrees per minute in the first minute after turning on was determined using a linear fit and is represented in FIG. 6. The dry tooth shows faster heating as no energy is required to evaporate the water. This effect can be used for an intelligent, individual end-of-treatment determination as claimed in the claims. In this way, the bacterial removal laser can be switched off if the measured temperature rise (ΔT/t) is greater than a predetermined threshold value which is in particular greater than the temperature rise in a wet treatment volume and at most as great as the temperature rise in a dry treatment volume.

Figure 7:
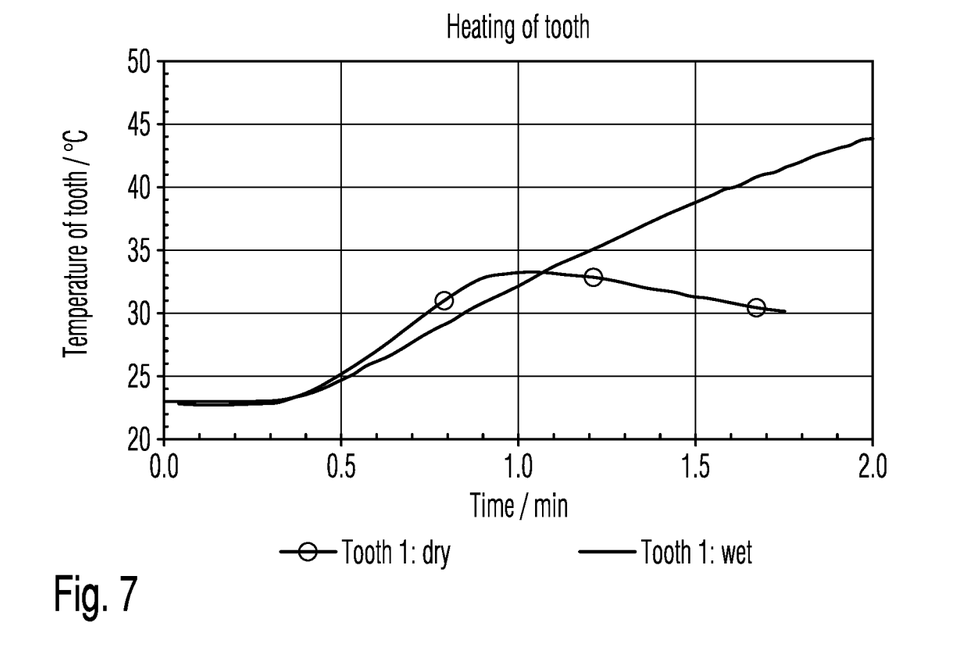
FIG. 7 shows the temperature of a wet tooth and a dry tooth measured by the temperature sensor.

FIG. 7 shows the heating curve of a tooth. The temperature rise of a wet tooth and a dry tooth is shown herein.

It is to be seen that the temperature gradient in time of the dry tooth is clearly higher, the energy application having been interrupted after approximately one minute, after the evaluation has revealed that all moisture—including bacteria—had vanished therefrom.

In another preferred embodiment, a target beam of visible light is provided concurrently with the laser beam. Through this it becomes visible to the dentist where he is treating.

In some embodiments, a processor can be a single processor having one or more cores, or a plurality of processors connected by a bus, network, or other data link. An electronic data storage unit can be any form of non-transitory computer-readable storage medium suitable for storing the data produced by the system.

In some embodiments, the device may linked to a camera, processor, electronic data storage unit, and digital display are components of a single device. The single device may be a smartphone, tablet, laptop computer, personal digital assistant, or other computing device.

In some embodiments, a processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Some embodiments may involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, a personal computer microprocessor, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A bacteria removal laser for the removal of caries bacteria on natural or prosthetic teeth comprising
   a gripping handle,
   an optical system with a predetermined beam exit surface, wherein the optical system comprises a radiation guide rod through which laser radiation passes,
   a laser radiation source, wherein the laser radiation source is configured to emit in the wavelength range between 2200 nm and 4000 nm, and is formed as an Er:YAG laser having an energy output of less than 1 mJ/mm$^2$ at the beam exit surface,
   a power source,
   a sensor configured to measure temperature of a treatment surface comprising teeth, and
   a control device connected to the sensor and configured to switch the laser radiation source off or reduce the radiation energy of the laser radiation source if a measured temperature increase ΔT/t of the teeth is greater than a temperature increase in a wet treatment volume and at most as great as a temperature increase in a dry treatment volume.

2. The bacteria removal laser according to claim 1, wherein the sensor responds to radiation in the wavelength range between 1000 nm and 15000 nm and has a sensitivity maximum above or below an emission maximum of the laser radiation source.

3. The bacterial removal laser according to claim 2, wherein the sensor is designed as a reflection detection sensor, and radiation reflected from the treatment surface can be detected by the sensor and wherein the reflected radiation is capable of passing through the optical system.

4. The bacterial removal laser according to claim 2, wherein the sensor is designed as a transmission detection sensor and radiation which passes through the treatment surface is detectable by the sensor.

5. The bacterial removal laser according to claim 1, wherein laser radiation pulsed with the laser radiation source is configured to emit with a pulse/pause ratio between 1:1 and 1:1000, with a power averaged over time of less than 2 W.

6. The bacteria removal laser according to claim 1, wherein laser radiation pulsed with the laser radiation source is configured to emit with a period duration between 0.02 s and 0.002 s, comprising an averaged power of less than 2 W, and a switching device for switching the laser radiation source on and off with a frequency of less than 1 Hz, and/or a treatment surface protection device, protecting the treatment surface from the radiation, with which the treatment surface is protectable from the radiation for a predetermined or adjustable or controllable time.

7. The bacteria removal laser according to claim 6, wherein the treatment surface protection device comprises an iris diaphragm or a mirror which is movable in front of the beam exit surface.

8. The bacteria removal laser according to claim 1, wherein radiation of the treatment surface which is reflected, transmitted or emitted is detectable by the sensor during pulse pauses.

9. The bacteria removal laser according to claim 1, wherein the beam exit surface and/or the treatment surface has a diameter of between 3 and 5 mm and wherein the bacteria removal laser has a light source with visible light, which is configured to emit visible light in addition to the laser radiation source and is guidable across the beam exit surface and is projectable onto the treatment surface and the latter being illuminated.

10. The bacteria removal laser according to claim 1, comprising
a sterile water source,
wherein the laser radiation source is coupled with the sterile water source with which the treatment surface is wettable with sterile water after the laser is switched off, but not during the switched-on state of the laser.

11. The bacterial removal laser according to claim 1, wherein laser radiation pulsed with the laser radiation source is configured to emit with a pulse/pause ratio between 1:5 and 1:200, with a power averaged over time of less than 2 W.

12. The bacterial removal laser according to claim 1, wherein laser radiation pulsed with the laser radiation source is configured to emit with a pulse/pause ratio between of about 1:25, with a power averaged over time of about 0.8 Watt.

13. The bacteria removal laser according to claim 1, wherein laser radiation pulsed with the laser radiation source is configured to emit with a period duration between 0.02 s and 0.002 s, comprising an averaged power of less than 2 W, and a switching device for switching the laser radiation source on and off with a frequency of less than about 0.3 Hz.

* * * * *